(12) United States Patent
Hedman

(10) Patent No.: US 9,101,602 B2
(45) Date of Patent: *Aug. 11, 2015

(54) USE OF NON-TOXIC CROSSLINKING REAGENTS TO IMPROVE FATIGUE RESISTANCE AND REDUCE MECHANICAL DEGRADATION OF INTERVERTEBRAL DISC AND OTHER COLLAGENOUS TISSUES

(75) Inventor: Thomas P. Hedman, Lexington, KY (US)

(73) Assignee: Orthopeutics L.P., Lexington, KY (US)

( * ) Notice: Subject to any disclaimer, the term of this patent is extended or adjusted under 35 U.S.C. 154(b) by 565 days.

This patent is subject to a terminal disclaimer.

(21) Appl. No.: 12/966,812

(22) Filed: Dec. 13, 2010

(65) Prior Publication Data

US 2011/0082199 A1    Apr. 7, 2011

Related U.S. Application Data

(63) Continuation of application No. 10/230,671, filed on Aug. 29, 2002.

(60) Provisional application No. 60/316,287, filed on Aug. 31, 2001.

(51) Int. Cl.
| | | |
|---|---|---|
| A61K 31/353 | (2006.01) | |
| A61K 31/70 | (2006.01) | |
| A61K 31/352 | (2006.01) | |
| A61K 31/7048 | (2006.01) | |

(52) U.S. Cl.
CPC .............. *A61K 31/353* (2013.01); *A61K 31/70* (2013.01); *A61K 31/7048* (2013.01)

(58) Field of Classification Search
USPC ....................................................... 514/456
See application file for complete search history.

(56) References Cited

U.S. PATENT DOCUMENTS 6,375,672 B1 *   4/2002   Aksan et al. .................... 607/96

FOREIGN PATENT DOCUMENTS

WO          WO 98/19718   *   5/1998 .............. A61L 15/18

OTHER PUBLICATIONS

Paper 133 from Interference No. 105,653.
Paper 168 from Interference No. 105,653.
Paper 173 from Interference No. 105,653.
Aug. 27, 2013 Notice of Appeal to the Federal Circuit.
Mar. 22, 2012 Federal Circuit Decision.
Interference Decision in related U.S. Appl. No. 10/230,671, Paper 82, Nov. 13, 2009.
Interference Decision in related U.S. Appl. No. 10/230,671, Paper 133, Nov. 23, 2010.
Interference Decision in related U.S. Appl. No. 10/230,671, Paper 168, Feb. 28, 2013.
Interference Order in related U.S. Appl. No. 10/230,671, Paper 169, Feb. 28, 2013.
Judgment on appeal of Board decision in related U.S. Appl. No. 10/230,671, Court of Appeals for the Federal Circuit, Nov. 10, 2014.
Appellants Brief to the Court of Appeals for the Federal Circuit in related U.S. Appl. No. 10/230,671, May 12, 2014.
Appellees Response Brief to the Court of Appeals for the Federal Circuit in related U.S. Appl. No. 10/230,671, Jul. 10, 2014.
Appellants Reply Brief to the Court of Appeals for the Federal Circuit in related U.S. Appl. No. 10/230,671, Aug. 7, 2014.
Recent patent case from the Court of Appeals for the Federal Circuit indicating that collateral estoppel does not necessarily apply to related patent applications, *eDigital Corp.* v. *Futurewei Technologies, Inc.*, Case No. 14-1019.

* cited by examiner

*Primary Examiner* — Ganapathy Krishnan
(74) *Attorney, Agent, or Firm* — Berliner & Associates

(57) ABSTRACT

A method of improving the resistance of collagenous tissue to mechanical degradation in accordance with the present invention comprises the step of contacting at least a portion of a collagenous tissue with an effective amount of a crosslinking reagent. The crosslinking reagent includes a crosslinking agent such as genipin and/or proanthrocyanidin. Further, the crosslinking reagent may include a crosslinking agent in a carrier medium. The collagenous tissue to be contacted with the crosslinking reagent is preferably a portion of an intervertebral disc or articular cartilage. The contact between the tissue and the crosslinking reagent is effected by injections directly into the select tissue using a needle. Alternatively, contact between the tissue and the crosslinking reagent is effected by placement of a time-release delivery system such as a gel or ointment, or a treated membrane or patch directly into or onto the target tissue. Contact may also be effected by, for instance, soaking.

14 Claims, 1 Drawing Sheet

USE OF NON-TOXIC CROSSLINKING REAGENTS TO IMPROVE FATIGUE RESISTANCE AND REDUCE MECHANICAL DEGRADATION OF INTERVERTEBRAL DISC AND OTHER COLLAGENOUS TISSUES

CROSS-REFERENCE TO RELATED APPLICATION

This application is a continuation of application Ser. No. 10/230,671, filed on Aug. 29, 2002, which claims the benefit of U.S. Provisional Application No. 60/316,287, filed Aug. 31, 2001.

BACKGROUND OF THE INVENTION

1. Field of the Invention

The present invention relates to a method for treatment of tissue, for example, collagenous tissue, where a deleterious mechanical loading environment contributes to the degradation of the tissue. More specifically, the present invention relates to a method for treatment of degenerated intervertebral discs to improve fatigue resistance, and to non-toxic crosslinking reagents that are effective fatigue inhibitors.

2. Description of the Related Art

Back pain and disability associated with spinal degeneration and instability continue to be one of the costliest and most prevalent health problems in western civilization. Current treatments for spinal instability and low-back pain, including spinal fusion, are generally ineffective in slowing the progression of degeneration. Epidemiological and morphological studies have shown that the capacity of spinal tissue to withstand repetitive loading is one critically important factor in the progression of spinal osteoarthritis (Magora 1972, Kelsey 1975, Frymoyer 1983, Videman 1990).

The organization of collagen and proteoglycans within the intervertebral disc plays an important role in determining the biomechanical properties of the disc. Biochemical alterations in the structure of the annular matrix affect the disc's durability, that is, its ability to withstand repetitive mechanical loading. Previous studies have shown that nonreducible pyridinoline cross links are predominant in adult cartilage, bone, and intervertebral discs and these collagen crosslinks are thought to be critical for the structural integrity (enzymatic and mechanical) of adult connective tissue (Burgeson and Nimni, 1992, Eyre, 1988). Pentosidine crosslinking has been shown to increase with age in articular cartilage and intervertebral discs (Bank 1998, Pokharna 1998).

A role for naturally occurring crosslinks in stabilizing degenerating discs has been suggested. Duance (1998) noted that while the nonenzymic derived crosslink pentosidine showed an expected age related increase, its level was lower in the more severely degenerated samples. It may be that age related tissue changes—i.e. micro-damage accumulation—combined with inadequate levels of crosslinks made these discs more vulnerable to mechanical degradation. Age related crosslinks (pentosidine) have been shown to increase the strength and stiffness of articular cartilage (Chen 2001) while age related microdamage accumulation would act to decrease strength and stiffness. With regard to viscoelastic properties, Lee (1989) found that aldehyde fixation (crosslinking) reduced stress-relaxation and creep in bovine pericardium, while fatigue loading produced an increase in stress-relaxation and creep in our preliminary testing of intervertebral discs.

Crosslinking reagents are capable of improving the tensile properties of collagen-based biomaterials. Osborne et al (1998) found mechanical strength of acellular collagen gels was most improved using a combination of crosslinking agents. Other researchers have also found that crosslinking treatments can increase the strength of collagenous tissues (Wang 1994, Chachra 1996, Sung 1999, Zeeman 1999). Sung (1999) found that a naturally occurring cross linking agent, genipin, provided greater ultimate tensile strength and toughness when compared with other crosslinking reagents. Genipin also demonstrated significantly less cytotoxicity compared to other more commonly used crosslinking agents. However it also stood out in a negative sense with regard to eliminating tissue anisotropy in bovine pericardium. Several researchers have stated their expectation that crosslinking of collagenous tissue may make, the tissue more prone to fatigue failure (Bank 1998, Chen 2001, Kerin 2001). However, it is believed that the opposing view—that crosslinking collagenous tissue may actually benefit fatigue resistance—has not been recorded in the medical literature. It is believed that collagen crosslinks may act as sacrificial bonds to protect collagenous tissues by dissipating energy and improving fatigue resistance.

Fatigue is a weakening of a material due to repetitive applied stress. Fatigue failure is simply a failure where repetitive stresses have weakened a material such that it fails below the original ultimate stress level. In bone, two processes—biological repair and fatigue—are in opposition, and repair generally dominates. In the intervertebral disc, the prevalence of mechanical degradation of the posterior annulus (Osti 1992) suggests that fatigue is the dominant process. Active tissue response (adaptation, repair) does not play a strong role in the case of mature intervertebral disc annular material. As a principally avascular structure, the disc relies on diffusion for nutrition of its limited number of viable cells. Age related changes interfere with diffusion presumably contributing to declining cell viability and biosynthetic function (Buckwalter et al. 1993, Buckwalter 1995). Age related decline in numbers of cells and cell functionality compromises the ability of the cells to repair mechanical damage to the matrix. While regeneration of the matrix in the nucleus following enzymatic degradation has been accomplished, albeit inconsistently (Deutman 1992), regeneration of functional annular material has not yet been realized.

Combined with this limited potential for repair or regeneration, studies have shown that posterior intervertebral disc tissue is vulnerable to degradation and fatigue failure when subjected to non-traumatic, physiologic cyclic loads. Prior work has shown deterioration in elastic-plastic (Hedman 99) and viscoelastic (Hedman 00) material properties in posterior intervertebral disc tissue subjected to moderate physiological cyclic loading. Cyclic load magnitudes of 30% of ultimate tensile strength produced significant deterioration of material properties with as little as 2000 cycles. Green (1993) investigated the ultimate tensile strength and fatigue life of matched pairs of outer annulus specimens. They found that fatigue failure could occur in less than 10,000 cycles when the vertical tensile cyclic peak exceeded 45% of the ultimate tensile stress of the matched pair control. In addition, Panjabi et al (1996) found that single cycle sub-failure strains to anterior cruciate ligaments of the knee alter the elastic characteristics (load-deformation) of the ligament. Osti (1992) found that annular tears and fissures were predominantly found in the posterolateral regions of the discs. Adams (1982) demonstrated the propensity of slightly degenerated discs to prolapse posteriorly when hyperflexed and showed that fatigue failure might occur in lumbar discs as the outer posterior annulus is overstretched in the vertical direction while severely loaded in flexion. In an analytical study, interlaminar shear stresses, which can produce delaminations, have been found to be highest in the posterolateral regions of the disc (Goel 1995). These prior data indicate: 1) the posterior disc and posterior longitudinal ligament are at risk of degenerative changes, and that 2) the mechanism of degeneration can involve flexion fatigue.

To date, however, no treatments capable of reducing mechanical degradation to collagenous tissues currently exist. In fact, no other collagenous tissue fatigue inhibitors have been proposed. A need therefore exists for a method for improving the resistance of collagenous tissues in the human body to fatigue and for reducing the mechanical degradation of human collagenous tissues, in particular, the posterior annulus region of the intervertebral disc.

SUMMARY OF THE INVENTION

It is one object of the present invention to provide a method of improving the resistance of collagenous tissues in the human body to mechanical degradation by contacting the tissue with crosslinking reagents.

It is another object of the present invention to provide a method of curtailing the progressive mechanical degradation of intervertebral disc tissue by enhancing the body's own efforts to stabilize aging discs by increasing collagen crosslinks.

It is another object of the present invention to provide a method that uses crosslinking reagents with substantially less cytotoxicity compared to common aldehyde fixation agents in order to facilitate direct contact of these reagents to tissues in the living human body.

It is another object of the present invention to increase the crosslinking of disc annular tissue by directly contacting living human disc tissue with appropriate concentrations of a non-toxic crosslinking reagent (or a mixture of crosslinking reagents) such as genipin (a geniposide) or proanthrocyanidin (a bioflavonoid).

It is another object of the present invention to provide a treatment method for minimally invasive delivery of the non-cytotoxic crosslinking reagent such as injections directly into the select tissue using a needle or placement of a time-release delivery system such as a carrier gel or ointment, or a treated membrane or patch directly into or onto the target tissue.

It is another object of the present invention to a composition composed of non-toxic crosslinking reagents that can be used as effective fatigue inhibitors.

In accordance with the present invention, there is provided a method for treatment of tissues where a deleterious mechanical loading environment contributes to the degradation of the tissue. The deleterious mechanical loading environment may consist of normal physiological repetitive loading, otherwise known as fatigue. The present invention provides a method for treatment of degenerated intervertebral discs to improve fatigue resistance. The present invention also provides non-toxic crosslinking compositions that are effective fatigue inhibitors.

A method of improving the resistance of collagenous tissue to mechanical degradation in accordance with the present invention comprises the step of contacting at least a portion of a collagenous tissue with an effective amount of a crosslinking reagent. The crosslinking reagent includes a crosslinking agent such as genipin and/or proanthrocyanidin. Further, the crosslinking reagent may include a crosslinking agent in a carrier medium. The collagenous tissue to be contacted with the crosslinking reagent is preferably a portion of an intervertebral disc or articular cartilage. The contact between the tissue and the crosslinking reagent is effected by injections directly into the select tissue using a needle. Alternatively, contact between the tissue and the crosslinking reagent is effected by placement of a time-release delivery system such as a gel or ointment, or a treated membrane or patch directly into or onto the target tissue. Contact may also be effected by, for instance, soaking or spraying.

DETAILED DESCRIPTION OF THE INVENTION

Figure 1:
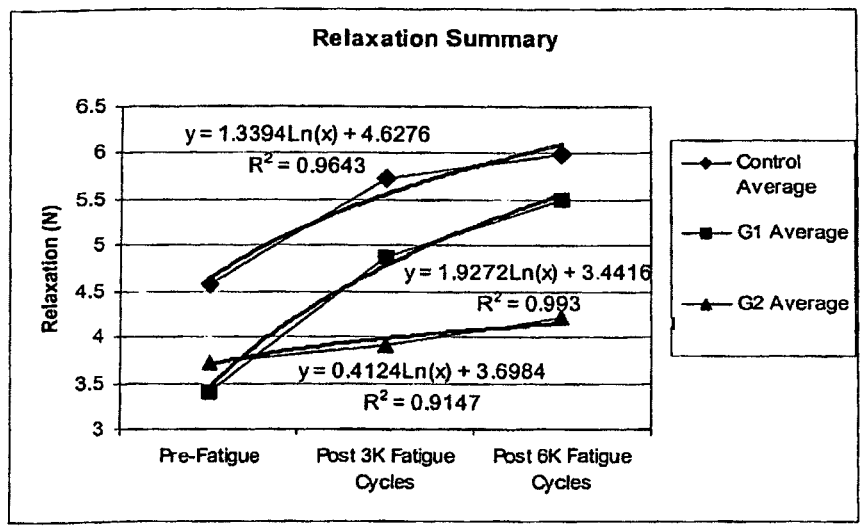
FIG. 1 is a graph of relaxation (N) v. numbers of cycles showing the effect of genipin crosslinking treatments (G1=0.033 g/mol, G2=0.33 g/mol) on posterior intervertebral disc stress relaxation.

The present invention provides a method of improving the resistance of collagenous tissues in the human body to mechanical degradation comprising the step of contacting at least a portion of a collagenous tissue with an effective amount of a crosslinking reagent. The method of the present invention also provides a method of curtailing the progressive mechanical degradation of intervertebral disc tissue by enhancing the body's own efforts to stabilize aging discs by increasing collagen crosslinks. This mechanical degradation may be in response to physiologic levels of repetitive loading.

The crosslinking reagent of the present invention is not particularly limited. Any crosslinking reagent known to be substantially non-cytotoxic and to be an effective cross-linker of collagenous material may be used. The crosslinking reagent is required to be substantially non-cytotoxic in order to facilitate direct contact of the crosslinking agent to tissues in the living human body. Preferably, the crosslinking reagent exhibits substantially less cytotoxicity compared to common aldehyde fixation agents. More preferably, a non-cytotoxic crosslinking reagent is used.

The crosslinking reagent includes at least one crosslinking agent. The crosslinking agent chosen in accordance with the present invention is an effective cross-linker of collagenous material. When used in a cross-linking reagent, an effective crosslinker is one that increases the number of crosslinks in the collagenous tissue when the crosslinker is brought into contact with a portion of the collagenous tissue. An effective crosslinker improves the fatigue resistance of the treated tissue, reduces material property degradation resulting from repetitive physiologic loading, or reduces the increase of viscoelastic properties of the treated tissue due to fatigue loading. Likewise, an effective crosslinker may reduce the decrease in elastic-plastic properties due to fatigue loading of the treated tissue. In one embodiment of the present invention, the crosslinking agent is Genipin, a non-toxic, naturally occurring crosslinking agent. Genipin is obtained from its parent compound, geniposide, which may be isolated from the fruits of *Gardenia jasminoides*. Genipin may be obtained commercially from Challenge Bioproducts Co., Ltd., 7 Alley 25, Lane 63, TzuChiang St. 404 Taichung Taiwan R.O.C., Tel 886-4-3600852. In another embodiment of the present invention, the crosslinking agent is a bioflavonoid, and more specifically, the bioflavonoid is proanthrocyanidin. A mixture containing proanthrocyanidin can be obtained as MegaNatural™ Gold from Polyphenolics, Inc, 22004 Rd. 24, Medera, Calif. 93638, Tel 559-637-5961. More than one crosslinking agent may be used.

The crosslinking reagent may include a carrier medium in addition to the crosslinking agent. The crosslinking agent may be dissolved or suspended in the carrier medium to form the crosslinking reagent. In one embodiment, a crosslinking agent is dissolved in a non-cytotoxic and biocompatible carrier medium. The carrier medium is required to be substantially non-cytotoxic in order to mediate the contact of the crosslinking agent to tissues in the living human body without substantial damage to the tissue or surrounding tissue. Preferably, the carrier medium chosen is water, and more preferably, a saline solution. Preferably, the pH of the carrier medium is adjusted to be the same or similar to the tissue environment. Even more preferably, the carrier medium is buffered. In one embodiment of the present invention, the carrier medium is a phosphate buffered saline (PBS).

When the crosslinking agent is dissolved in a carrier medium, the concentration of the crosslinking agent in the carrier medium is not particularly limited. The concentration may be in any amount effective to increase the crosslinking of the tissue while at the same time remaining substantially noncytotoxic. When the crosslinking agent is genipin, the concentration of the crosslinking agent is preferably greater than 0.033% in PBS (wt %), and more preferably, about 0.33% in PBS (wt %).

In accordance with the present invention, the crosslinking reagent is brought into contact with a portion of a collagenous tissue. As used herein, collagenous tissue is defined to be a structural or load supporting tissue in the body comprised of a substantial amount of collagen. Examples would include intervertebral disc, articular cartilage, ligament, tendon, bone, and skin. In general, the portion of the collagenous tissue to be brought into contact with the crosslinking reagent is the portion of the tissue that is subject to loading. Further, where at least some degradation of the collagenous tissue has occurred, the portion of the tissue to be contacted with the crosslinking reagent is at least the portion of the tissue that has been degraded. Preferably, the entire portion that is subject to loading or the entire portion that is degraded is contacted with the crosslinking reagent. Further, the tissue adjacent the portion of collagenous tissue subject to the loading may also be contacted with the crosslinking reagent.

The collagenous tissues that are particularly susceptible for use in accordance with the present invention include intervertebral discs and articular cartilage. Where the collagenous tissue is an intevertebral disc, the portion of the intervertebral disc that is preferably contacted by the crosslinking reagent is the posterior and posterolateral annulus fibrosis.

The selected portion of the collagenous tissue must be contacted with an effective amount of the non-toxic crosslinking reagent. An "effective amount" is an amount of crosslinking reagent sufficient to have a mechanical effect on the portion of the tissue treated. Specifically, an "effective amount" of the crosslinking reagent is an amount sufficient to improve the fatigue resistance of the treated tissue, reduce material property degradation resulting from repetitive physiologic loading, or reduce the increase of viscoelastic properties of the treated tissue due to fatigue loading, or reduce the decrease of elastic-plastic properties of the treated tissue due to fatigue loading. An effective amount may be determined in accordance with the viscoelastic testing and/or the elastic-plastic testing described herein with respect to Examples 1 and 2.

The method of the present invention includes contacting at least a portion of the collagenous tissue with an effective amount of the crosslinking reagent. The contact may be effected in a number of ways. Preferably, the contacting of collagenous tissue is effected by a means for minimally invasive delivery of the non-cytotoxic crosslinking reagent. Preferably, the contact between the tissue and the crosslinking reagent is effected by injections directly into the select tissue using a needle. Preferably, the contact between the tissue and the crosslinking reagent is effected by injections from a single or minimum number of injection locations. Preferably, an amount of crosslinking solution is injected directly into the targeted tissue using a needle and a syringe. Preferably, a sufficient number of injections are made along the portion of the tissue to be treated so that complete coverage of the portion of the collagenous tissue to be treated is achieved.

Alternatively, contact between the tissue and the crosslinking reagent is effected by placement of a time-release delivery system directly into or onto the target tissue. One time-released delivery system that may be used is a treated membrane or patch. A reagent-containing patch may be rolled into a cylinder and inserted percutaneously through a cannula to the tissue sight, unrolled and using a biological adhesive or resorbable fixation device (sutures or tacks) be attached to the periphery of the targeted tissue.

Another time-released delivery system that may be used is a gel or ointment. A gel or ointment is a degradable, viscous carrier that may be applied to the exterior of the targeted tissue.

Contact also may be effected by soaking or spraying, such as intra-capsular soaking or spraying, in which an amount of crosslinking solutions could be injected into a capsular or synovial pouch.

It should be noted that the methods and compositions treated herein are not required to permanently improve the resistance of collagenous tissues in the human body to mechanical degradation. Assuming that a person experiences 2 to 20 upright, forward flexion bends per day, the increased resistance to fatigue associated with contact of the collagenous tissue with the crosslinking reagent, may, over the course of time, decrease. Preferably, however, the increased resistance to fatigue lasts for a period of several months to several years without physiologic mechanical degradation. Under such circumstance, the described treatment can be repeated at the time periods sufficient to maintain an increased resistance to fatigue resistance. Using the assumption identified above, the contacting may be repeated periodically to maintain the increased resistance to fatigue. For some treatment, the time between contacting is estimated to correspond to approximately 1 year for some individuals. Therefore, with either a single treatment or with repeated injections/treatments, the method of the present invention minimizes mechanical degradation of the collagenous tissue over an extended period of time.

Examples 1 and 2

Thirty-three lumbar intervertebral joints were obtained from ten four-month-old calf spines. The intervertebral joints were arbitrarily divided into 3 groups: untreated controls-12 specimens, Genipin treatment 1 (G1)-6 specimens, and Genipin treatment 2 (G2)-13 specimens. The G1 treatment involved 72 hours of soaking the whole specimen in PBS with a 0.033% concentration of Genipin.

Similarly the G2 treatment involved 72 hours of soaking whole specimens in PBS with 0.33% concentration of Genipin. 0.33% Genipin in PBS is produced by dilution of 50 ml of 10×PBS (Phosphate Buffered Saline) with distilled water by a factor of 10 to give 500 ml (500 gm) of PBS and mixing in 1.65 grams of genipin to produce the 0.33% (wt %, gm/gm) solution. Previous testing with pericardium and tendon tissue samples demonstrated the reduction of tissue swelling (osmotic influx of water into the tissue) resulting from crosslinking the tissue. Some controls were not subjected to soaking prior to fatigue testing. Others were soaked in a saline solution for 72 hours. Water mass loss experiments were conducted to establish the equivalency of outer annulus hydration between the genipin soaked and 0.9% saline soaked controls. The selection of treatments was randomized by spine and level. The vertebral ends of the specimens were then potted in polyurethane to facilitate mechanical testing.

Indentation testing and compression/flexion fatigue cycling were carried out in the sequence presented in Table 1.

TABLE 1

Experimental protocol

| Measurement Sequence | Measurement | Location |
|---|---|---|
| 1 | Stress Relaxation | Center of the Posterior Annulus |
| 2 | Hardness | Center of the Posterior Annulus |
| | 3000 Compression/Flexion Fatigue Cycles | |
| 3 | Stress Relaxation | 4 mm Lateral to Center |
| 4 | Hardness | Center of the Posterior Annulus |
| | Additional 3000 Compression/Flexion Fatigue Cycles | |
| 5 | Stress Relaxation | 4 mm Lateral to Center (Opposite Side) |
| 6 | Hardness | Center of the Posterior Annulus |

At the prescribed points in the loading regimen, indentation testing was used to find viscoelastic properties as follows. Stress relaxation data was gathered by ramp loading the 3 mm diameter hemi-spherical indenter to 10 N and subsequently holding that displacement for 60 s, while recording the resulting decrease in stress, referred to as the stress relaxation. Indentation testing was also utilized to determine elastic-plastic properties by calculating a hardness index (resistance to indentation) from ramp loading data. Prior to recording hardness measurements, the tissue is repeatedly indented 10 times (60 s/cycle, to the displacement at an initial 10 N load).

This test protocol is based on two principles. First, viscoelastic effects asymptotically decrease with repeated loading. Secondly, hardness measurements are sensitive to the loading history of the tissue. However this effect becomes negligible following 10 loading cycles. In order to minimize these effects, viscoelastic data (stress relaxation) was collected from tissue that had not previously been indented. Alternately, elastic-plastic data (hardness) was collected from tissue that had been repeatedly loaded (preconditioned). In this case, repetitive indentation was intended to reduce the undesired effects of the changing viscoelastic properties, namely lack of repeatability, on hardness measurements. These testing procedures were derived from several preliminary experiments on the repeatability of the measurements with variations of loading history and location.

Following initial indentation testing, the specimen was loaded repetitively in flexion-compression at 200 N for 3000 cycles at a rate of 0.25 Hz. The load was applied perpendicularly to the transverse plane, 40 mm anterior to the mid-point of the specimen in the transverse plane. A second set of indentation testing data is then collected following fatigue cycling. This procedure was followed for two fatigue loading cycles. During all testing, the specimens were wrapped in saline wetted gauze to maintain their moisture content. Fatigue cycling and non-destructive indentation testing were carried out on an MTS 858.02 biaxial, table-top, 10 kN capacity servo-hydraulic materials test station (MTS, Eden Prairie, Minn.), with the MTS Test Star data acquisition system. Several statistical measures were calculated to evaluate the significance of the results. A nested two-way analysis of variance (ANOVA) was utilized to confirm effects due to treatment and number of fatigue cycles. Due to the non-parametric nature of the data, the Mann-Whitney non-parametric rank-sum test was used to assess the null hypotheses that the treatment did not affect: 1) the pre-cycling mechanical parameters of the tissue, or 2) the amount of change (degradation) in elastic-plastic and viscoelastic mechanical parameters due to fatigue loading. The confidence level for statistical significance was set at $p<0.05$.

Nested two-way ANOVA analysis determined that both viscoelastic (relaxation) and elastic-plastic (hardness) mechanical parameters were independently affected by fatigue cycling and by treatment type. These statistical results are presented in Table 2.

The relaxation test results are presented graphically in FIG. 1. There was an initial shift downward of the relaxation curve caused by the crosslinking treatment. This would represent a beneficial effect as higher stress relaxation would be associated with more severely degraded tissue (Lee 1989). The initial pre-fatigue relaxation of the G1 and G2 treatment groups were 26% and 19% less than ($p=0.009$ and $p=0.026$) the pre-fatigue relaxation of the controls respectively. There was also dramatic improvement in fatigue resistance as demonstrated by the change in relaxation after 6000 non-traumatic loading cycles. The change in relaxation due to 6000 fatigue cycles for the G2 treated discs was less than a third of the change in the controls ($p=0.044$). However, the lesser concentration of Genepin did not bring about the same improvement in fatigue resistance.

Figure 2:
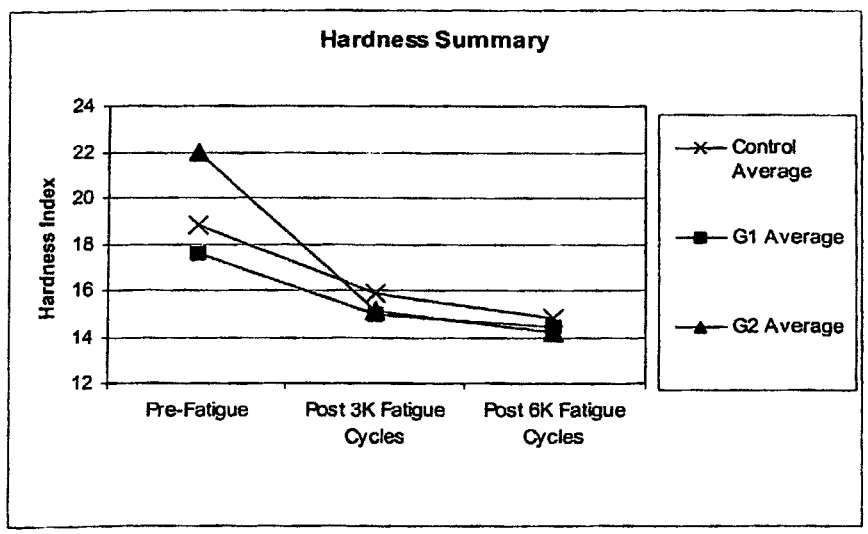
FIG. 2 is a graph of Brinnell's hardness index v. numbers of cycles showing the effect of genipin crosslinking treatments (G1=0.033 g/mol, G2=0.33 g/mol) on posterior intervertebral disc hardness or resistance to penetration.

The hardness test results are presented graphically in FIG. 2. There is an initial shift upward of the hardness data caused by the G2 crosslinking treatment. This would represent a beneficial effect as loss of hardness would signal a loss of structural integrity in the tissue. The initial pre-fatigue hardness of the G2 treatment group was 17% greater than that of the control group ($p=0.026$). However this beneficial effect appears to have eroded prior to 3000 fatigue cycles and the change in hardness between 3000 and 6000 cycles is essentially the same for the two groups (G2=−0.94, Control=−1.01).

TABLE 2

Results of nested two-way ANOVA analysis

| Material Property | Factor | F-Value | Probability |
|---|---|---|---|
| Stress Relaxation | Treatment | 16.060 | 1.085E−06 |
| | Fatigue Cycling | 9.676 | 2.500E−03 |
| | Interaction | 1.402 | 2.515E−01 |
| Hardness | Treatment | 20.023 | 6.405E−08 |
| | Fatigue Cycling | 5.898 | 1.710E−02 |
| | Interaction | 4.228 | 1.760E−02 |

The data presented above quantifies the elastic and viscoelastic mechanical degradation of intervertebral disc tissue due to repetitive, non-traumatic loading. The results of these experiments establish that non-toxic crosslinking reagents reduce the fatigue-related degradation of material properties in a collagenous tissue—namely the intervertebral disc. More than a three-fold reduction in viscoelastic degradation was brought about by soaking the calf disc tissue in 0.33 g/mol concentration of genipin. The tested formulation was unable to sustain an improvement in the elastic mechanical properties (hardness) to 3000 test cycles.

Accurately estimating the length of time it would take an average person to experience a comparable amount of wear and tear on their spinal discs is difficult. Certainly, in addition to the mechanical degradation imposed by the described testing, there is the added—"natural"—degradation of these dead tissues due to the testing environment. The non-loaded controls showed this "natural" degradation of material properties to be insignificant. Measures were taken to minimize this natural degradation by keeping the specimens moist throughout the testing and by accelerating the loading frequency. At the same time, loading frequency was kept within physiologic limits to prevent tissue overheating. It should be noted that these measures constitute standard protocol for in vitro mechanical testing of cadaveric tissues. Assuming that a person experiences 2 to 20 upright, forward flexion bends per day, these data roughly correspond to several months to several years of physiologic mechanical degradation.

The described treatment could be repeated at the time periods represented by, for instance, 3000 fatigue cycles at this load magnitude. Using the assumption identified above, this number of cycles may be estimated to correspond to approximately 1 year for some individuals. Therefore, with either a single treatment or with repeated injections/treatments, an individual may be able to minimize mechanical degradation of their intervertebral discs over an extended period of time. Another option would involve a time-release delivery system such as a directly applied treated patch, a gel or ointment.

The invention has been described in terms of certain preferred and alternate embodiments which are representative of only some of the various ways in which the basic concepts of the invention may be implemented. Certain modification or variations on the implementation of the inventive concepts which may occur to those of ordinary skill in the art are within the scope of the invention and equivalents, as defined by the accompanying claims.

LIST OF REFERENCES

Adams, M A, Green, T P, Dolan, P, The strength in anterior bending of lumbar intervertebral discs, Spine, 19:2197-2203, 1994.

Adams, M A, Hutton, W C, Prolapsed intervertebral disc—a hyperflexion injury, Spine, 7:184-191, 1982.

Bank, R A, Bayliss, M T, Lafeber, F P J G, Maroudas, A, Tekoppele, J M, Ageing and zonal variation in post-translational modification of collagen in normal human articular cartilage: The age-related increase in non-enzymatic glycation affects biomechanical properties of cartilage, *Biochem. J.*, 330:345-351, 1998.

Biering-Sorensen, F, A prospective study of low back pain in a general population. I. Occurrence, recurrence and aetiology, *Scandinavian Journal of Rehabilitation Medicine*, 15:71-79, 1983

Buckwalter, J A, Aging and degeneration of the human intervertebral disc, *Spine*, 20:1307-1314, 1995.

Buckwalter, J A, Woo, S L-Y, Goldberg, V M, Hadley, E C, Booth, F, Oegema, T R, Eyre, D R, Current concepts review. Soft-tissue aging and musculoskeletal function, *Journal Bone Joint Surgery*, 75A:1533-1548, 1993.

Burgeson, R E, Nimni, M E, Collagen types. Molecular structure and tissue distribution. [Review], *Clinical Orthopaedics & Related Research*, (282):250-72, 1992

Chachra, D, Gratzer, P F, Pereira, C A, Lee, J M, Effect of applied uniaxial stress on rate and mechanical effects of cross-linking in tissue-derived biomaterials, Biomaterials, 17:1865-75, 1996

Chen, A C, Temple, M M, Ng, D M, Richardson, C D, DeGroot, J, Verzijl, N, teKoppele, J M, Sah, R L, Age-related cross linking alters tensile properties of articular cartilage, *Orthopaedic Research Society Transactions*, 26:0128, 2001.

Deutman, R, The case for chemonucleolysis in discogenic sciatica. A review., *Acta Orthopaedica Scandinavia*, 63:571-575, 1992.

Duane, V C, Crean, J K G, Sims, T J, Avery, N, Smith, S, Menage, J, Eisenstein, S M, Roberts, S, Changes in collagen cross-linking in degenerative disc disease and scoliosis, *Spine*, 23:2545-2551, 1998.

Eyre D R, Dickson I R, VanNess K, Collagen cross-linking in human bone and articular cartilage, *Biochem J*, 252:495-500, 1988.

Farfan, H F, Huberdeau, R M, Dubow, H I, Lumbar intervertebral disc degeneration, *J. Bone Jt Surg.*, 54A:492-510, 1972.

Frymoyer, J W, Pope, M H, Clements, J H, Wilder, D G, MacPherson, B, Ashikaga, T, Risk factors in low-back pain, *Journal Bone and Joint Surgery*, 65A:213-218, 1983.

Glazier, R, Fry, J, Badley, E, Arthritis and rheumatism are neglected health priorities: A bibliometric study, *Journal of Rheumatology*, 28:706-711, 2001.

Goel, V K, Monroe, B T, Gilbertson, L G, Brinckmann, P, Interlaminar shear stresses and laminae separation in a disc, *Spine*, 20:689-698, 1995.

Green, T P, Adams, M A, Dolan, P, Tensile properties of the annulus fibrosus. II. Ultimate tensile strength and fatigue life, *European Spine Journal*, 2:209-214, 1993.

Hedman, T P, Fernie, G R, Mechanical response of the lumbar spine to seated postural loads, *Spine*, 22:734-743, 1997.

Hedman, T P, Liao, W L, Yu, J, Watkins, R, Liker, M, Strength reduction of the posterior intervertebral disc resulting from repetitive sub-failure loading, *Orthopaedic Research Society Transactions*, 24:1017, 1999.

Hedman, T P, Use of non-destructive materials testing techniques to assess the degradation of intervertebral discs subjected to non-traumatic repetitive loads, *Presented at the USC/GOS Annual Meeting*, Los Angeles, Calif., Jun. 22-23, 2000.

Hirsch, C, Schajowicz, F, Studies on structural changes in the lumbar annulus fibrosus, *Acta Orthop. Scand.*, 22:184-231, 1953.

Kelsey, J L, An epidemiological study of acute herniated lumbar discs, *Rheumatology and Rehabilitation*, 14:144-159, 1975.

Kerin, A, Hung, G, Verzijl, N, DeGroot, J, TeKoppele, J, Grodzinsky, A, The effect of non-enzymatic glycation on mechanical properties of articular cartilage, *Orthopaedic Research Society Transactions*, 26:0130, 2001.

Klein, B P, Jensen, R C, Sanderson, L M, Assessment of workers' compensation claims for back strains/sprains, *J Occup Med*, 26:443-448, 1984.

Lee, J M, Haberer, S A, Boughner, D R, The bovine pericardial xenograft: I. Effect of fixation in aldehydes without constraint on the tensile viscoelastic properties of bovine pericardium, *Journal of Biomedical Materials Research*, 23:457-475, 1989.

Magora, A, Investigation of the relation between low back pain and occupation: sitting, standing and weight lifting, *Industrial Medicine*, 41:5-9, 1972.

Osborne, C S, Barbenel, J C, Smith, D, Savakis, M, Grant, M H, Investigation into the tensile properties of collagen/chondroitin-6-sulphate gels: the effect of crosslinking agents and diamines, *Med. Biol. Eng. Comput.*, 36:129-134, 1998.

Osti, O L, Vernon-Roberts, B, Moore, R, Fraser, R D, Annular tears and disc degeneration in the lumbar spine: a post-mortem study of 135 discs, *J. Bone Jt Surg.,* 74B:678-682, 1992.

Panjabi, M M, Yoldas, E, Oxland, T R, Crisco, J J, Subfailure injury of the rabbit anterior cruciate ligament, J. Orthop. Res., 14:216-222, 1996.

Pokharna, H K, Phillips, F M, Collagen crosslinks in human lumbar intervertebral disc aging, Spine, 23(15):1645-1648, 1998.

Sung, H W, Chang, Y, Chiu, C T, Chen, C N, Liang, H C, Crosslinking characteristics and mechanical properties of a bovine pericardium fixed with a naturally occurring crosslinking agent, *Journal Biomed. Materials Res.,* 47:116-126, 1999.

Sung, H W, Huang, R N, Huang, L L, Tsai, C C, In vitro evaluation of cytotoxicity of a naturally occurring crosslinking reagent for biological tissue fixation, *Journal of Biomaterials Science, Polymer Edition,* 10:63-78, 1999.

Videman, T, Nurminen, M, Troup, J D G, Lumbar spinal pathology in cadaveric material in relation to history of back pain, occupation, and physical loading, *Spine,* 15:728-738, 1990.

Waddell, G, Low back pain: A twentieth century health care enigma, *Spine,* 21:2820-2825, 1996.

Wang, X D, Masilamani, N S, Mabrey, J D, Alder, M E, Agrawal, C M, Changes in the fracture toughness of bone may not be reflected in its mineral density, porosity, and tensile properties, *Bone,* 23:67-72, 1998.

Zeeman, R, Dijkstra, P J, van Wachem, P B, van Luyn, M J, Hendriks, M, Cahalan, P T, Feijen, J, Crosslinking and modification of dermal sheep collagen using 1,4-butanediol diglycidyl ether, *Journal of Biomedical Materials Research,* 46(3):424-33, 1999

I claim:

1. A method of improving the resistance of a collagenous tissue having naturally occurring cross links to mechanically-induced degradation comprising the steps of:
    contacting at least a portion of a load bearing collagenous tissue within a human body with an effective amount of a crosslinking reagent comprised of a carrier medium and at least one crosslinking agent under conditions within physiologic limits to prevent tissue overheating, wherein the collagenous tissue is an intervertebral disc.

2. The method of claim 1, wherein the at least one crosslinking agent is comprised of genipin.

3. The method of claim 1, wherein the at least one crosslinking agent is comprised of proanthocyanidin.

4. The method of claim 1, wherein the crosslinking agent is selected from the group consisting of genipin and proanthocyanidin and the carrier medium is a buffered saline solution.

5. The method of claim 1, wherein the crosslinking agent is genipin, the carrier medium is a buffered saline solution, and a concentration of the genipin in the buffered saline solution is greater than 0.033%.

6. The method of claim 1, wherein the contact between the collagenous tissue and the crosslinking reagent is effected by injections directly into the portion of the collagenous tissue with a needle.

7. The method of claim 1, wherein the contact between the collagenous tissue and the crosslinking reagent is effected by placement of a time-release delivery system directly into or onto the portion of the collagenous tissue.

8. The method of claim 7, wherein the time-release delivery system is a gel or ointment.

9. The method of claim 7, wherein the time-release delivery system is a treated membrane or patch.

10. The method of claim 7, wherein the time-release delivery system is a treated patch.

11. The method of claim 1, wherein the contact between the collagenous tissue and the crosslinking reagent is effected by soaking.

12. The method of claim 1, wherein the contact between the collagenous tissue and the crosslinking reagent is effected by spraying.

13. The method of claim 1, further comprising the step of contacting collagenous tissue adjacent to the load bearing collagenous tissue.

14. The method of claim 1, further comprising the step of:
    periodically re-contacting the portion of the collagenous tissue with an effective amount of a crosslinking reagent.

* * * * *